US006228822B1

(12) United States Patent
Allison et al.

(10) Patent No.: US 6,228,822 B1
(45) Date of Patent: May 8, 2001

(54) SYNTHETIC DETERGENT BASE MATERIAL AND SYNTHETIC DETERGENT BAR PRODUCED THEREFROM

(75) Inventors: William C. Allison, Murrysville; Lorna Alderfer, Export, both of PA (US)

(73) Assignee: BASF Corporation, Mount Olive, NJ (US)

( * ) Notice: Subject to any disclaimer, the term of this patent is extended or adjusted under 35 U.S.C. 154(b) by 0 days.

(21) Appl. No.: 08/437,712

(22) Filed: May 9, 1995

(51) Int. Cl.[7] .......... A61K 7/50

(52) U.S. Cl. .......... 510/153; 510/141; 510/152; 510/155; 510/156

(58) Field of Search .......... 252/108, 121, 252/117, 173.14

(56) References Cited

U.S. PATENT DOCUMENTS

| | | | | |
|---|---|---|---|---|
| 2,987,484 | | 6/1961 | Lundberg et al. | 252/174 |
| 3,879,309 | * | 4/1975 | Gatti et al. | 252/117 |
| 4,329,824 | * | 5/1982 | Kacher et al. | 252/108 |
| 4,673,525 | | 6/1987 | Small et al. | 252/132 |
| 4,812,253 | * | 3/1989 | Small et al. | 252/132 |
| 5,075,623 | * | 12/1991 | Lundberg et al. | 252/108 |
| 5,096,608 | | 3/1992 | Small et al. | 252/132 |
| 5,186,855 | | 2/1993 | Crudden | 252/117 |
| 5,225,097 | | 7/1993 | Kacher et al. | 252/112 |
| 5,284,598 | | 2/1994 | Subrmanyam et al. | 252/121 |

FOREIGN PATENT DOCUMENTS

| | | |
|---|---|---|
| 1 477 897 | 6/1977 | (GB) . |
| WO 92/16610 | 10/1992 | (WO) . |

* cited by examiner

*Primary Examiner*—Necholus Ogden
(74) *Attorney, Agent, or Firm*—David T. Banchik

(57) ABSTRACT

Described are novel synthetic detergent base materials having a pH from 5 to 8 and consisting essentially of from 45 to 70 weight percent of mild synthetic surfactant, salts thereof, or a mixture of the mild synthetic surfactant and salts thereof; from 20 to 30 weight percent of $C_8$–$C_{22}$ fatty acid; from 1.5 to 10 weight percent of $C_8$–$C_{22}$ n-acyl sarcosine, salts thereof, or a mixture of the sarcosine and salts thereof; from 0.5 to 5 weight percent of $C_1$–$C_{22}$ alkyl aryl sulfonic acid, salts thereof, or a mixture of the sulfonic acid and salts thereof; and from 1 to 5 weight percent soap, e.g., salts of $C_8$–$C_{22}$ fatty acid. Also described are syndet bars prepared from the synthetic detergent base material.

18 Claims, No Drawings

SYNTHETIC DETERGENT BASE MATERIAL AND SYNTHETIC DETERGENT BAR PRODUCED THEREFROM

DESCRIPTION OF THE INVENTION

The present invention relates to a synthetic detergent base material, and synthetic detergent bars produced using the synthetic detergent base material. More particularly, this invention relates to a synthetic detergent base material consisting essentially of mild synthetic surfactant and/or salts thereof, $C_8$–$C_{22}$ fatty acids, $C_8$–$C_{22}$ n-acyl sarcosine and/or salts thereof, $C_1$–$C_{22}$ alkyl aryl sulfonic acid and/or salts thereof, and soap, i.e., salts of $C_8$–$C_{22}$ fatty acids; and synthetic detergent bars containing the synthetic detergent base material.

Synthetic detergent bars, frequently referred to as "syndet bars", are well known and are becoming increasingly popular. However, syndet bars have not replaced soap bars widely for a variety of reasons. One reason is that syndet bars, as compared to soap bars, are softer and smear more easily, i.e., partially dissolve or form a gel, with use.

Mild synthetic surfactant formulations that contain n-acyl sarcosine have been described in U.S. Pat. No. 5,096,608 and International Patent publication WO 92/16610. Detergent bars containing mild synthetic surfactant, e.g. acyl isethionate, and alkyl aryl sulfonate have been disclosed in U.S. Pat. No. 3,879,309 and British Patent 1477897. The combined use of alkyl aryl sulfonate and n-acyl sarcosine in a mild synthetic surfactant formulation has not been disclosed.

A process for producing a synthetic detergent soap base with n-acyl sarcosine is disclosed in U.S. Pat. No. 5,186,855. This process involves the neutralization of n-acyl sarcosine at an elevated temperature with a fatty acid salt to the desired pH. A process for making mild, detergent-soap toilet bars containing acyl isethionate as the principal surfactant is described in U.S. Pat. No. 5,284,598. This process incorporates a vegetable oil that reduces the viscosity of a liquid detergent-soap mixture making it readily pumpable, as compared to the mixture prepared in the absence of the vegetable oil.

It has now been discovered that a synthetic detergent base material, which combines a desirably high level of active ingredients, i. e., up to 85 weight percent total synthetic surfactant, and a low hot melt viscosity, which enables easy preparation of base material without special processing equipment, can be prepared. The synthetic detergent base material may be used with conventional adjuvant materials in skin cleansing compositions, e.g., bars, gels, pastes and liquids. Such formulations provide the desired physical properties associated with soap bars, such as acceptable bar smear, i.e., a rating of from 3 to 8 in the Hewitt Soap Company Method No. 107, and acceptable bar hardness properties, i.e., a rating from 30 to 90, using a Precision Universal Penetrometer and the procedure described in association with the Examples. This synthetic detergent base consists essentially of from 45 to 70 weight percent of mild synthetic surfactant (or mixtures of mild synthetic surfactants), from 20 to 30 weight percent of $C_8$–$C_{22}$ fatty acid; from 1.5 to 10 weight percent of $C_8$–$C_{22}$ n-acyl sarcosine, salts thereof or a mixture of the n-acyl sarcosine and salts thereof; from 0.5 to 5 weight percent of $C_1$–$C_{22}$ alkyl aryl sulfonic acid, salts thereof or a mixture of the sulfonic acid and salts thereof; and from 1 to 5 weight percent salt(s) of $C_8$–$C_{22}$ fatty acid. The pH of the synthetic detergent base ranges typically from 5 to 8, preferably from 5.5 to 7 and more preferably from 6 to 6.5. A syndet bar containing this detergent base and conventional soap bar adjuvant materials can be prepared using standard bar processing equipment.

DETAILED DESCRIPTION OF THE INVENTION

In accordance with the present invention, there is provided a synthetic detergent base material having a pH from 5 to 8 and consisting essentially of from 45 to 70 weight percent of mild synthetic surfactant (or mixtures of mild synthetic surfactants); from 20 to 30 weight percent of $C_8$–$C_{22}$ fatty acid; from 1.5 to 10 weight percent of $C_8$–$C_{22}$ n-acyl sarcosine, salt(s) thereof, or a mixture of the sarcosine and salt(s) thereof; from 0.5 to 5 weight percent of $C_1$–$C_{22}$ alkyl aryl sulfonic acid, salt(s) thereof, or a mixture of the sulfonic acid and salt(s) thereof; and from 1 to 5 weight percent salt of $C_8$–$C_{22}$ fatty acid. The pH of the synthetic base material is determined by measuring the pH of a 10 weight percent aqueous solution of the base material. As used herein and in the claims, the pH of the base material is understood to mean the pH of a 10 weight percent aqueous solution. All numbers expressing quantities of ingredients, weight ratios, or reaction conditions used herein and in the claims are to be understood as modified in all instances by the term "about", except in the operating examples or where otherwise indicated. Also, all percentages used herein and in the claims are weight percents, unless otherwise noted, and are to be understood as based on the weight of the total composition of the material being described, e.g., the synthetic detergent base material and the synthetic detergent bar.

As used herein and in the claims, the term, mild synthetic surfactant, is intended to mean and include those surfactants which have a Relative Skin Barrier Penetration Value, as described in U.S. Pat. No. 5,096,608 at column 4, line 46 to column 6, line 44, of from near zero to about 75. Further, the term mild synthetic surfactant includes cosmetically acceptable salts of such surfactants. By cosmetically acceptable is meant that the salt may be used in cosmetic preparations, such as syndet bars. Examples of salts include the sodium, potassium, magnesium, ammonium, monoethanolammonium, diethanolammonium and triethanolammmonium salts and mixtures of such salts.

Examples of mild synthetic surfactants include alkyl glyceryl ether sulfonates, methyl acyl taurates, n-acyl glutamates, alkyl glucosides, trideceth sulfates, i.e., sulfated ethoxylated tridecyl alcohol, acyl isethionates, alkyl sulfosuccinates, alkyl phosphate esters, ethoxylated alkyl phosphate esters, methyl glucose esters, mixtures of ethoxylated alkyl sulfates and alkyl amine oxides, betaines, sultaines and cosmetically acceptable salts of such mild surfactants. Mixtures of such mild surfactants and/or the salts thereof may also be used. The alkyl and acyl groups for these mild surfactants typically contain from 8 to 22 carbon atoms ($C_8$–$C_{22}$). The degree of ethoxylation for these mild surfactants, e.g., the alkyl ether sulfates, such as ammonium and sodium lauryl ether sulfate, generally have an average of from 1 to 12 ethoxy groups.

Preferably, the amount of mild synthetic surfactant present in the synthetic base material ranges from 45 to 60 weight percent. More preferably, the mild synthetic surfactant represents from 50 to 60 weight percent of the base material and is selected from the group consisting of sodium and/or ammonium salts of acyl isethionates, e.g., sodium cocoyl isethionate, ammonium cocoyl isethionate and mixtures of such cocoyl isethionates. Commercially available sources of sodium cocoyl isethionate may be formulated with stearic acid and typically also contain minor amounts of sodium isethionate and coconut fatty acid.

The synthetic detergent base further contains from 20 to 30 weight percent of fatty acid. The lipophilic portion of the fatty acid may comprise alkyl-, alkenyl-, or hydroxyalkenyl-groups containing from about 8 to 22 carbon atoms, preferably from about 8 to 18 carbon atoms. The carbon chain may be linear, branched, even or odd numbered, saturated and unsaturated. When the fatty acid is derived from natural animal or vegetable sources, the acids generally comprise a mixture of the aforementioned lipophilic groups. For example, distilled mixed vegetable oil fatty acid may have the following carbon-chain distribution: 3 percent lauric fatty acid, 10–12 percent myristic acid, 15–20 percent palmitic acid, 18–25 percent stearic acid, 45–50 percent oleic acid and 5 percent linoleic acid.

The fatty acid may be derived from an animal, e.g., beef tallow, or vegetable, e.g., coconut, palm, and soybean, source or produced by synthetic routes. The synthesis of acids having a similar carbon chain length as fatty acids may be achieved by using petroleum feedstocks in the Oxo or Ziegler processes to produce aldehydes or alcohols, respectively, which when subjected to further oxidation form the corresponding acids.

Preferably, the amount of fatty acid present in the base material ranges from 22 to 28 weight percent and are selected from the group consisting of coconut fatty acid, tallow fatty acid, and caprylic, capric, lauric, myristic, palmitic, and stearic acids, and mixtures of such fatty acids, e.g. tallow/coconut fatty acid mixtures. More preferably, the fatty acid is present in the base material in an amount of from 24 to 26 weight percent.

The $C_8$–$C_{22}$ n-acyl sarcosine, salt(s) thereof or mixtures of such sarcosine and mixtures of such sarcosine salts may be present in the synthetic detergent base in amounts of from 1.5 to 10 weight percent. Preferred acyl sarcosines are selected from the group consisting of lauroyl sarcosine, cocoyl sarcosine, myristoyl sarcosine, stearoyl sarcosine, and oleoyl sarcosine. Salts of the sarcosines may be selected from the group consisting of sodium salts, monoethanolammonium salts, diethanolammonium salts, triethanolammonium salts, ammonium salts, potassium salts, magnesium salts and mixtures of such salts. Preferably, the sarcosine component of the base material is present in amounts of from 2 to 8 weight percent, more preferably, from 4 to 7 weight percent. Preferably, the sarcosine and salts thereof are selected from the group consisting of lauroyl sarcosine, cocoyl sarcosine, sodium salts thereof, and mixtures of such sarcosines and their sodium salts.

The $C_1$–$C_{22}$ alkyl aryl sulfonic acid, salts thereof, or mixtures of such sulfonic acids and mixtures of salts of sulfonic acids may be present in the synthetic detergent base in amounts of from 0.5 to 5 weight percent, preferably, from 1 to 3 weight percent, and more preferably from 2 to 3 weight percent. The aryl group may be phenyl or naphthyl, preferably phenyl. Suitable alkyl aryl sulfonic acids include xylene sulfonic acid, toluene sulfonic acid, hexyl benzene sulfonic acid, octyl benzene sulfonic acid, nonyl benzene sulfonic acid, decyl benzene sulfonic acid, dodecyl benzene sulfonic acid, methyl naphthalene sulfonic acid, hexyl naphthalene sulfonic acid, octyl naphthalene sulfonic acid, nonyl naphthalene sulfonic acid, decyl naphthalene sulfonic acid, and dodecyl naphthalene sulfonic acid. The alkyl aryl sulfonic acid may be present in the base material as the free acid, as a salt of the acid or as a mixture of the free acid and salt. If the salt of the sulfonic acid is not added to the base material, it may be formed during pH adjustment of the base material, or as a result of a neutralization occurring during the preparation of the base material from other base materials included with the other compounds. Salts of the alkyl aryl sulfonic acids may include sodium salts, monoethanolammonium salts, diethanolammonium salts, triethanolammonium salts, ammonium salts, potassium salts, magnesium salts and mixtures of such salts.

Preferably, the $C_1$–$C_{22}$ alkyl aryl sulfonic acid is selected from the group consisting of xylene sulfonic acid, toluene sulfonic acid, hexyl benzene sulfonic acid, octyl benzene sulfonic acid, nonyl benzene sulfonic acid, decyl benzene sulfonic acid, and dodecyl benzene sulfonic acid. Preferred salts of the alkyl aryl sulfonic acid include sodium and potassium salts.

Soap, i.e., salts of $C_8$–$C_{22}$ fatty acids, is present in the synthetic detergent base material in amounts from 1 to 5 weight percent. Suitable salts include sodium salts, monoethanolammonium salts, diethanolammonium salts, triethanolammonium salts, ammonium salts, potassium salts, magnesium salts and mixtures of such salts. Preferably, the soap is present in amounts of from 1 to 3 weight percent and is a sodium salt.

The synthetic detergent base material typically contains a small amount of water, usually less than 2 weight percent. This water is present in the ingredients used to prepare the base material or is adsorbed from the atmosphere by hygroscopic ingredients in the base material. Additional water is added to the base material during processing to prepare the syndet bar. In embodiments contemplated herein, the weight ratio in the syndet bar of total synthetic surfactant, i.e., the combined amounts of mild synthetic surfactants and $C_1$–$C_{22}$ alkyl aryl sulfonic acid (including salts of the alkyl aryl sulfonic acid) to fatty acid salts, i.e., soap, may range from 10:1 to 85:1, preferably, from 15:1 to 70:1, and more preferably, from 20:1 to 35:1. The weight ratio in the syndet bar of $C_1$–$C_{22}$ alkyl aryl sulfonic acid (including salts thereof) to $C_8$–$C_{22}$ n-acyl sarcosine (including salts thereof), may range from 3:1 to 1:20, preferably, 2:1 to 1:8, and more preferably, from 1.5:1 to 1:3.

The synthetic detergent base material of the present invention may be prepared by the steps of:

(a) combining the $C_8$–$C_{22}$ n-acyl sarcosine and/or salts thereof, mild synthetic surfactant, $C_8$–$C_{22}$ fatty acid and salts thereof, and $C_1$–$C_{22}$ alkyl aryl sulfonic acid in a suitable mixing vessel;

(b) heating the resultant mixture to liquify and form a uniform liquid mixture of these components, e.g., by heating the mixture with mixing at temperatures in the range of from 80 to 125° C.;

(c) adjusting, if necessary, the pH of the product of step (b), e.g., to within the range of from about 5 to about 8, preferably from 5.5 to 7 and more preferably from 6 to 6.5, by adding an alkaline reagent to the mixture, and (d) cooling the mixture to form a solid product.

As a result of pH adjustment with an alkaline reagent, acidic starting materials, e.g., $C_1$–$C_{22}$ alkyl aryl sulfonic acid and n-acyl sarcosine may form their corresponding salts. Suitable alkaline reagents that may be used include ammonium, sodium and/or potassium hydroxide, or such salts of a $C_8$–$C_{22}$ fatty acid. In the event that the mixture becomes too alkaline, the pH can be adjusted downward with an appropriate acid, e.g., isethionic acid.

The solid product produced from step (d) may be in various physical forms, e.g., granulated, flaked and fragmented. Granulated material may be produced by cooling the uniform mixture in, for example, a ribbon blender and continuing the mixing operation to breakdown the solids into granules. Flaked material may be prepared by cooling the uniform mixture on a chill roller or a drum dryer and removing the solid product with a knife or scraper that results in the formation of flakes or chips. Fragmented material may be prepared by cooling the uniform mixture in containers such as shallow trays and subsequently breaking up the resulting solid pieces into fragments of the desired size. Preferably, the product is produced in the flaked material form.

Synthetic detergent bars made from the base composition of the present invention may be prepared by methods known in the art, e.g., see U.S. Pat. No. 5,096,608 column 9, line 44 to column 10, line 63. It will be understood by those skilled in the art that conventional adjuvant materials commonly added to soap bars may be added to the detergent base materials. Examples of such adjuvant materials include extenders, such as modified food starches, urea, clays, talc, and the like; salts, such as sodium chloride, metallic stearates, and hydrogenated vegetable glyceride phosphates to improve processing properties; and other conventional additives, such as fragrance, antioxidants, chelating agents, foam stabilizers, dyes, germicides, etc. Many of these additives are optional ingredients which are added in minor quantities and which do not materially effect the viscosity of base material mixture. Water will be present in the syndet bar in amounts usually in the range of 2 to 10, e.g., 3.5 to 9, weight percent.

The salts of the various components of the synthetic detergent base material, whether added as such or formed in situ, are preferably selected from the group consisting of sodium salts, monoethanolammonium salts, diethanolammonium salts, triethanolammonium salts, ammonium salts, potassium salts, magnesium salts and mixtures of such salts.

The present invention is more particularly described in the following examples which are intended as illustrative only since numerous modifications and variations therein will be apparent to those skilled in the art.

EXAMPLE

In the following examples, materials listed in Table 1 for each of the examples were added to a Littleford, Model M-5-G blender. The blender was operated at a rotational speed setting of about 3 to 4. After all of the materials were added, mixing was continued for about 2 hours while a temperature of about 105° C. was maintained by a Sterl-Tronic Temperature Controller. The viscosity of this hot melt during preparation was rated by the operator on a scale from 1 to 5, 1 being more fluid and 5 being the most viscous. The temperature of the batch was than reduced to 35° C. Dry ice was added in an amount sufficient to complete the conversion of the liquid to a solid phase, e.g., from about 300 grams to about 1000 grams of dry ice. The resulting solid was subsequently broken up in the blender. The viscosity ratings and pH values of the blend are listed in Table 2.

The synthetic detergent base material blend was added to a ribbon blender and the ingredients listed in Table 3 were added. The resulting mixture was blended for about 5 to 10 minutes at room temperature. The resulting blended product was added to a Mazzoni M-100 Simplex Refiner/Plodder maintained at a temperature of about 30 to 40° C. The product was successively forced or refined through a 20 mesh screen 3 times, a 30 mesh screen 3 times, and a 50 mesh screen 3 times. Afterwards, the refined product was added to a Mazzoni M-100 Simplex Refiner/Plodder having a nosecone heated to about 50 to 60° C. and an extrusion plate in place of the screens. The billet exiting the extrusion plate was cut into slugs about 3.5 to 4 inches in length. Each slug was pressed into a bar using a Mazzoni STL hand press. Each step of the bar forming process, i.e., refining, extruding, and pressing, was rated on a scale of 1 to 3, 1 being difficult and 3 being easy. These ratings are listed in Table 4.

TABLE 1

| | Components (grams) | | | | | | | | | |
|---|---|---|---|---|---|---|---|---|---|---|
| Example No. | Cocoyl Sarcosine | Lauroyl Sarcosine | DDBSA[1] | Sodium DDBSA | Sodium Stearate | Sodium Glycinate | Stearic Acid | Jordapon ® CI-75[2] | Jordapon ® CI-P[3] | Soap[4] |
| 1 | 183 | — | 57 | — | — | — | — | 2088 | — | 327 |
| 2 | 189 | — | 60 | — | — | — | — | 1410 | 744 | 336 |
| 3 | — | 189 | 60 | — | 336 | — | — | 1638 | 516 | — |
| 4 | — | 135 | — | 63 | 213 | — | 60 | 1872 | 405 | — |
| 5 | 132 | — | — | 63 | 207 | — | — | 2052 | 216 | — |
| 6 | — | 132 | — | 63 | — | 90 | 123 | 2340 | — | — |
| 7 | — | 66 | — | 63 | 132 | — | — | 2328 | 90 | — |
| 8 | — | 63 | — | 126 | 132 | — | — | 2328 | 15 | — |
| 9 | — | 132 | — | 63 | 207 | — | — | 2052 | 216 | — |
| CE*-1 | — | — | — | 60 | 90 | — | 300 | 1200 | 858 | 255 |
| CE*-2 | — | — | — | 63 | 73 | — | — | 2465 | 71 | — |

[1]Dodecyl benzene sulfonic acid

[2]Approximately 65 weight percent sodium cocoyl isethionate and 25 weight percent stearic acid, the remainder being coconut fatty acid and sodium isethionate.

[3]A powder that is approximately 85 weight percent sodium cocoyl isethionate, based on the total composition, the remainder being coconut fatty acid and sodium isethionate.

[4]Approximately an 80/20 weight percent mixture of the sodium salts of tallow fatty acid/coconut fatty acid.

CE*—Comparative Example.

TABLE 2

| Viscosity rating and pH of hot melt. | | |
|---|---|---|
| Example No. | Viscosity Rating | pH |
| 1 | 2 | 6.3 |
| 2 | 4–5 | 6.6 |
| 3 | 3 | 6.5 |
| 4 | 3–4 | 6.4 |

TABLE 2-continued

Viscosity rating and pH of hot melt.

| Example No. | Viscosity Rating | pH |
|---|---|---|
| 5 | 4 | 6.4 |
| 6 | 1–2 | 6.3 |
| 7 | 4 | 6.1 |
| 8 | 3.5–4 | 6.3 |
| 9 | 3 | 6.1 |
| CE*-1 | 5 | 7.1 |
| CE*-2 | 5 | 6.3 |

The pH of each Example was determined by measuring the pH of a 10 weight percent aqueous solution of the base material.

The results in Table 2 show a reduction in viscosity for the hot melts having either cocoyl sarcosine or lauroyl sarcosine and sodium dodecyl benzene sulfonic acid (DDBSA) as compared to the Comparative Examples 1 and 2 having only DDBSA.

TABLE 3

Ingredients (grams)

| Example No. | NaCl | Hampol 120[5] | Fragrance | BHT[6] | $TiO_2$ | Water |
|---|---|---|---|---|---|---|
| 1 | 60 | — | — | — | — | 193 |
| 2 | 60 | — | — | — | — | 190.4 |
| 3 | 60 | — | — | — | — | 190.4 |
| 4 | — | — | — | — | — | 195.5 |
| 5 | 33.6 | 7.8 | 20.8 | 1.3 | 13 | 203.3 |
| 6 | 19.2 | 7.8 | 20.8 | 1.3 | 13 | 97.8 |
| 7 | 12 | 7.8 | 20.8 | 1.3 | 13 | 95.2 |
| 8 | 19.2 | 7.8 | 20.8 | 1.3 | 13 | 100.3 |
| 9 | 33.6 | 7.8 | 20.8 | 1.3 | 13 | 203.3 |
| CE*-1 | — | — | — | — | — | 203.3 |
| CE*-2 | 19.2 | 7.8 | 20.8 | 1.3 | 13 | 159.5 |

[5]Approximately a 50 weight percent aqueous solution of trisodium N-hydroxyethyl ethylenediaminetriacetate.
[6]Butylated hydroxytoluene

TABLE 4

Bar finishing step ratings.

| Example No. | Refining | Extruding | Stamping |
|---|---|---|---|
| 1 | 1 | 2 | 2 |
| 2 | 2–3 | 3–4 | 4 |
| 3 | 2 | 2 | 2 |
| 4 | 3 | 3 | 3 |
| 5 | 3 | 3 | 2 |
| 6 | 2–3 | 2–3 | 2 |
| 7 | 3 | 3 | 2 |
| 8 | 3 | 3 | 3 |
| 9 | 3 | 3 | 3 |
| CE*-1 | 2–3 | 3 | 3 |
| CE*-2 | 3 | 2 | 2 |

The results in table 4 show that the bar finishing rating of the examples is as good or better for Examples 2, 4, 5, 7, 8, and 9 as compared to the Comparative Examples 1 and 2.

The pressed bars were evaluated for bar hardness and bar smear. Bar hardness was determined using a Precision Universal Penetrometer and a modified procedure of that described in *Soap Technology For The* 1990*s* edited by Luis Spitz, 1990, published by the American Oil Chemists' Society, page 282. The procedure was modified by running 5 penetrations on one side of the bar, totaling the results and doing 5 more penetrations on the other side and totaling the results. The average of both totals is reported in Table 5. The bar smear test was done following the Hewitt Soap Company Method No. 107 described on pp. 278 to 279 in *Soap Technology For The* 1990*s*. These results are also reported in Table 5.

For each example, the weight percent, based on the total composition of the finished bar, of the total synthetic surfactant, e.g., the combined amount of sodium cocoyl isethionate, sodium cocoyl sarcosine, sodium lauroyl sarcosine and sodium dodecyl benzene sulfonic acid; soap, i.e., salts of fatty acids; and free fatty acids, i.e., stearic acid, coconut fatty acid and tallow fatty acid; are listed in Table 6. Also included in Table 6 is the weight ratio of synthetic detergent (A) to soap (S), synthetic detergent (A) to free fatty acid (FA), and free fatty acid (FA) to soap (S).

TABLE 5

Bar smear and hardness results.

| Example No. | Smear | Hardness |
|---|---|---|
| 1 | 8.5 | 52.0 |
| 2 | 6.0 | 45.0 |
| 3 | 10.15 | 25.75 |
| 4 | 5.61 | 30.25 |
| 5 | 7.37 | 114.25 |
| 6 | 3.2 | 78.0 |
| 7 | 8.6 | 34.0 |
| 8 | 5.9 | 38.75 |
| 9 | 3.5 | 76 |
| CE*-1 | 5.6 | 88.25 |
| CE*-2 | 3.7 | 48 |

The results in Table 5 show that the bar smear properties of Examples 2, 4, 5, 6, 7, 8, and 9 lie within the desired range of 3 to 8 as do the Comparative Examples 1 and 2. Results for bar hardness of Examples 1, 2, 4, 7, 8, and 9 lie within the desired range of 30 to 90 as do the Comparative Examples.

TABLE 6

Weight percent and weight ratios of selected finished bar components

| Example No. | Syn. Det. (A) | Soap (S) | Fatty Acid (FA) | A:S | A:FA | FA:S |
|---|---|---|---|---|---|---|
| 1 | 54.7 | 3.0 | 28.7 | 18.2:1 | 1.9:1 | 9.6:1 |
| 2 | 59.8 | 3.0 | 22.6 | 19.9:1 | 2.6:1 | 7.5:1 |
| 3 | 58.3 | 2.4 | 25.2 | 24.3:1 | 2.3:1 | 10.5:1 |
| 4 | 59.5 | 2.1 | 26.4 | 28.3:1 | 2.2:1 | 12.6:1 |
| 5 | 57.4 | 2.2 | 25.4 | 26.1:1 | 2.3:1 | 11.5:1 |
| 6 | 58.9 | 1.9 | 26.4 | 31.0:1 | 2.2:1 | 13.9:1 |
| 7 | 60.6 | 2.0 | 27.1 | 30.3:1 | 2.2:1 | 13.6:1 |
| 8 | 60.3 | 2.1 | 26.8 | 28.7:1 | 2.2:1 | 12.8:1 |
| 9 | 57.5 | 2.0 | 25.5 | 28.8:1 | 2.3:1 | 12.8:1 |
| CE*-1 | 53.3 | 11.8 | 23.9 | 4.5:1 | 2.2:1 | 2.0:1 |
| CE*-2 | 59.0 | 2.5 | 25.4 | 23.6:1 | 2.3:1 | 10.2:1 |

Although the present invention has been described with reference to the specific details of particular embodiments, it is not intended that such details be regarded as limitations upon the scope of the invention except as and to the extent that they are included in the accompanying claims.

We claim:

1. A synthetic detergent base material consisting essentially of:

(a) from 45 to 70 weight percent of mild synthetic surfactant other than (c);

(b) from 20 to 30 weight percent of $C_8$–$C_{22}$ fatty acid;

(c) from 1.5 to 10 weight percent of $C_8$–$C_{22}$ n-acyl sarcosine, salt(s) thereof or a mixture of said sarcosine and said salt(s);

(d) from 0.5 to 5 weight percent of $C_1$–$C_{22}$ alkyl aryl sulfonic acid, salt(s) thereof or a mixture of said sulfonic acid and said salt(s);

(e) from 1 to 5 weight percent salt(s) of $C_8$–$C_{22}$ fatty acid; and (f) less than 2 weight percent water; said synthetic detergent base material having a pH from 5 to 8.

2. The synthetic detergent base material of claim 1 wherein the salts of $C_1$–$C_{22}$ alkyl aryl sulfonic acid are selected from the group consisting of sodium salts, monoethanolammonium salts, diethanolammonium salts, triethanolammonium salts, ammonium salts, magnesium salts, potassium salts and mixtures of such salts.

3. The synthetic detergent base material of claim 1 wherein the salts of the $C_8$–$C_{22}$ n-acyl sarcosine, $C_8$–$C_{22}$ fatty acid and $C_1$–$C_{22}$ alkyl aryl sulfonic acid are each selected from the group consisting of sodium salts, monoethanolammonium salts, diethanolammonium salts, triethanolammonium salts, ammonium salts, magnesium salts, potassium salts and mixtures of such salts.

4. The synthetic detergent base material of claim 3 wherein the salts are sodium salts.

5. The synthetic detergent base material of claim 3 wherein:

(a) the $C_8$–$C_{18}$ fatty acid is selected from the group consisting of coconut fatty acids, tallow fatty acids, caprylic acid, capric acid, lauric acid, myristic acid, palmitic acid, stearic acid and mixtures of such acids;

(b) the $C_8$–$C_{22}$ n-acyl sarcosine is selected from the group consisting of lauroyl sarcosine, cocoyl sarcosine, myristoyl sarcosine, stearoyl sarcosine, and oleoyl sarcosine; and (c) the $C_1$–$C_{22}$ alkyl aryl sulfonic acid is selected from the group consisting of xylene sulfonic acid, toluene sulfonic acid, hexyl benzene sulfonic acid, octyl benzene sulfonic acid, nonyl benzene sulfonic acid, decyl benzene sulfonic acid, dodecyl benzene sulfonic acid, methyl naphthalene sulfonic acid, hexyl naphthalene sulfonic acid, octyl naphthalene sulfonic acid, nonyl naphthalene sulfonic acid, decyl naphthalene sulfonic acid, dodecyl naphthalene sulfonic acid, and mixtures of such sulfonic acids.

6. The synthetic detergent base material of claim 4 wherein the fatty acid salt is a sodium salt.

7. A synthetic detergent bar comprising soap bar adjuvants, from 2 to 10 weight percent water and a synthetic detergent base material consisting essentially of (a) mild synthetic surfactant (i) $C_8$–$C_{22}$ n-acyl sarcosine, salts thereof or a mixture of said n-acyl sarcosine and salts thereof, and (ii) at least mild synthetic surfactant other than, (b) from about 0.5 to about 5.0 weight percent of $C_1$–$C_{22}$ alkyl aryl sulfonic acid, salts thereof or a mixture of said sulfonic acid and salts thereof; (c) $C_8$–$C_{22}$ fatty acid; and (d) salts of $C_8$–$C_{22}$ fatty acid, wherein the weight ratio of the sum of components (a) plus (b) to component (d) ranges from about 10:1 to about 85.1; and the weight ratio of component (b) to component (a)(i) ranges from about 3:1 to about 1:20, said salts of said components (a), (b) and (d) being selected form the group consisting of sodium salts, monoethanolammonium salts, diethanolammonium salts, triethanolammonium salts, ammonium salts, potassium salts, magnesium salts and mixtures of said salts.

8. The synthetic detergent bar of claim 7 wherein said weight ratio of components (a) plus (b) to component (d) ranges from about 15:1 to about 70:1, and the weight ratio of component (b) to component (a)(i) ranges from about 2:1 to about 1:8.

9. The synthetic detergent bar of claim 8 wherein said weight ratio of components (a) plus (b) to component (d) ranges from about 20:1 to about 35:1 and the weight ratio of component (b) to component (a)(i) ranges from about 1.5:1 to about 1:3.

10. A synthetic detergent bar comprising the synthetic detergent base material of claim 5 and soap bar adjuvants.

11. The synthetic detergent base material of claim 1 wherein said salts of $C_8$–$C_{22}$ n-acyl sarcosine and $C_8$–$C_{22}$ fatty acid are selected from the group consisting of sodium salts, monoethanolammonium salts, diethanolammonium salts, triethanolammonium salts, ammonium salts, potassium salts, magnesium salts and mixtures of such salts.

12. The synthetic detergent base material of claim 1 wherein the salts of $C_1$–$C_{22}$ alkyl aryl sulfonic acid are selected from the group consisting of sodium salts, monoethanolammonium salts, diethanolammonium salts, triethanolammonium salts, ammonium salts, magnesium salts, potassium salts and mixtures of such salts; and said $C_8$–$C_{22}$ n-acyl sarcosine salts, and $C_8$–$C_{22}$ fatty acid salts are sodium salts.

13. The synthetic detergent base material of claim 1 wherein:

(a) the mild synthetic detergent is present in amounts of from 45 to 60 weight percent and is selected from the group consisting of $C_8$–$C_{22}$ alkyl glyceryl ether sulfonates, methyl $C_8$–$C_{22}$ acyl taurates, $C_8$–$C_{22}$ n-acyl glutamates, $C_8$–$C_{22}$ alkyl glucosides, trideceth sulfates, $C_8$–$C_{22}$ acyl isethionates, $C_8$–$C_{22}$ alkyl sulfosuccinates, $C_8$–$C_{22}$ alkyl phosphate esters, ethoxylated $C_8$–$C_{22}$ alkyl phosphates, methyl glucose esters, mixtures of ethoxylated $C_8$–$C_{22}$ alkyl sulfates and $C_8$–$C_{22}$ alkyl amine oxides, betaines, sultaines, and mixtures of said mild surfactants;

(b) the $C_8$–$C_{18}$ fatty acid is present in amounts of from 22 to 28 weight percent;

(c) the $C_8$–$C_{22}$ n-acyl sarcosine, salt(s) thereof, or a mixture of said sarcosine and salt(s) thereof is present in amounts of from 2 to 8 weight percent;

(d) the $C_1$–$C_{22}$ alkyl aryl sulfonic acid, salt(s) thereof, or a mixture of said sulfonic acid and salt(s) thereof is present in amounts of from 1 to 3 weight percent; and (e) the salt(s) of $C_8$–$C_{22}$ fatty acid is present in amounts of from 1 to 3 weight percent; said synthetic base material having a pH of from 5.5 to 7.

14. The synthetic detergent base material of claim 13 wherein:

(a) the mild synthetic surfactant is present in amounts of from 50 to 60 weight percent;

(b) the $C_8$–$C_{18}$ fatty acid is selected from the group consisting of coconut fatty acids, tallow fatty acids, caprylic acid, capric acid, lauric acid, myristic acid, palmitic acid, stearic acid and mixtures of such acids, and such acid is present in amounts of from 24 to 26 weight percent;

(c) the $C_8$–$C_{22}$ n-acyl sarcosine is selected from the group consisting of lauroyl sarcosine, cocoyl sarcosine, myristoyl sarcosine, stearoyl sarcosine, and oleoyl sarcosine and said acyl sarcosine is present amounts of from about 4 to 7 weight percent; and (d) the $C_1$–$C_{22}$ alkyl aryl sulfonic acid is present in amounts of from about 2 to 3 weight percent, said sulfonic acid being selected from the group consisting of xylene sulfonic acid, toluene sulfonic acid, hexyl benzene sulfonic acid, octyl benzene sulfonic acid, nonyl benzene sulfonic acid, decyl benzene sulfonic acid, dodecyl benzene sulfonic acid, methyl naphthalene sulfonic acid, hexyl naphthalene sulfonic acid, octyl naphthalene sulfonic acid, nonyl naphthalene sulfonic acid, decyl naphthalene sulfonic acid, dodecyl naphthalene sulfonic acid, and mixtures of such sulfonic acids; said synthetic base material having a pH from 6 to 6.5.

15. The synthetic detergent base material of claim 14 wherein said mild synthetic surfactant is a sodium salt of $C_8$–$C_{22}$ acyl isethionate, ammonium salt of said isethionate, or a mixture of said sodium and ammonium salts of $C_8$–$C_{22}$ acyl isethionate; said $C_8$–$C_{22}$ n-acyl sarcosine and salts thereof are selected from the group consisting of lauroyl sarcosine, cocoyl sarcosine, sodium salts thereof, and mixtures of said sarcosines and sodium salts thereof; and said $C_1$–$C_{22}$ alkyl aryl sulfonic acid is selected from the group consisting of xylene sulfonic acid, toluene sulfonic acid, hexyl benzene sulfonic acid, octyl benzene sulfonic acid, nonyl benzene sulfonic acid, decyl benzene sulfonic acid, dodecyl benzene sulfonic acid, and mixtures of said sulfonic acids, and sodium or potassium salts of said sulfonic acids.

16. A synthetic detergent bar comprising the synthetic detergent base material of claim 1 and soap bar adjuvants.

17. A synthetic detergent bar comprising the synthetic detergent base material of claim 1 and soap bar adjuvants.

18. A synthetic detergent bar comprising the synthetic detergent base material of claim 15 and soap bar adjuvants.

* * * * *